United States Patent
Hamamatsu et al.

(10) Patent No.: US 7,474,394 B2
(45) Date of Patent: Jan. 6, 2009

(54) APPARATUS OF INSPECTING DEFECT IN SEMICONDUCTOR AND METHOD OF THE SAME

(75) Inventors: Akira Hamamatsu, Yokohama (JP); Shunji Maeda, Yokohama (JP); Hisae Shibuya, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 10 days.

(21) Appl. No.: 11/488,622

(22) Filed: Jul. 19, 2006

(65) Prior Publication Data

US 2007/0019185 A1    Jan. 25, 2007

(30) Foreign Application Priority Data

Jul. 20, 2005    (JP)    ............................. 2005-209384

(51) Int. Cl.
*G01N 21/88* (2006.01)
(52) U.S. Cl. .............. 356/237.2; 356/237.1; 356/237.4; 250/559.41
(58) Field of Classification Search ... 356/237.1–237.6, 356/394, 392; 250/559.41, 559.29; 382/141, 382/149, 154
See application file for complete search history.

(56) References Cited

U.S. PATENT DOCUMENTS

| | | | | |
|---|---|---|---|---|
| 5,146,509 A | * | 9/1992 | Hara et al. .................. | 382/149 |
| 5,822,055 A | * | 10/1998 | Tsai et al. ................. | 356/237.1 |
| 6,167,355 A | * | 12/2000 | Fiekowsky ................... | 702/159 |
| 6,246,472 B1 | * | 6/2001 | Yoda et al. ................ | 356/237.2 |
| 6,246,787 B1 | * | 6/2001 | Hennessey et al. .......... | 382/141 |
| 6,256,092 B1 | * | 7/2001 | Tomita et al. ............. | 356/237.1 |
| 6,411,377 B1 | * | 6/2002 | Noguchi et al. .......... | 356/237.4 |
| 6,597,448 B1 | * | 7/2003 | Nishiyama et al. ........ | 356/237.4 |
| 6,797,975 B2 | | 9/2004 | Nishiyama et al. | |
| 6,816,249 B2 | * | 11/2004 | Fairley et al. ............. | 356/237.1 |
| 6,888,959 B2 | * | 5/2005 | Hamamatsu et al. ......... | 382/149 |
| 6,936,835 B2 | * | 8/2005 | Nishiyama et al. ..... | 250/559.41 |
| 7,271,921 B2 | * | 9/2007 | Shortt ......................... | 356/630 |

FOREIGN PATENT DOCUMENTS

JP    05-273110    10/1993
JP    2003-098111    4/2003

* cited by examiner

*Primary Examiner*—Sang Nguyen
(74) *Attorney, Agent, or Firm*—Antonelli, Terry, Stout & Kraus, LLP.

(57) ABSTRACT

When size of a defect on an increasingly miniaturized pattern is obtained by defect inspection apparatus in the related art, a value is inconveniently given, which is different from a measured value of the same defect by SEM. Thus, a dimension value of a defect detected by defect inspection apparatus needs to be accurately calculated to be approximated to a value measured by SEM. To this end, size of the defect detected by the defect inspection apparatus is corrected depending on feature quantity or type of the defect, thereby defect size can be accurately calculated.

13 Claims, 12 Drawing Sheets

FIG.2A scattering signal of defect A

FIG.2B scattering signal of defect B

[display sample of defect detection result]

APPARATUS OF INSPECTING DEFECT IN SEMICONDUCTOR AND METHOD OF THE SAME

BACKGROUND OF THE INVENTION

The present invention relates to defect inspection apparatus and a defect inspection method which are used in a manufacturing line of a semiconductor device, liquid crystal device, magnetic head or the like, and particularly relates to a calculation technique of size of a detected defect.

Inspection of a semiconductor wafer is described as an example.

In a semiconductor manufacturing process in the related art, foreign substances on a semiconductor substrate (wafer) may cause inferiority such as imperfect insulation or a short circuit. When a fine foreign substance exists in a semiconductor substrate of a semiconductor element which is significantly miniaturized, the foreign substance may cause imperfect insulation of a capacitor or breakdown of a gate oxide film. The foreign substances may be contaminated in various ways due to various reasons, such as contamination from a movable portion of a carrier device, contamination from a human body, contamination from reaction of a process gas in treatment equipment, and previous contamination in chemicals or materials. Similarly, in a manufacturing process of a liquid crystal display device, contamination of a foreign substance on a pattern, or formation of some defects disables the device as a display device. The same situation occurs in a manufacturing process of a printed circuit board, that is, contamination of the foreign substance leads to a short circuit of a pattern or imperfect connection.

It is now increasingly important to detect a defect such as foreign substance causing inferior products and take the measure for causes of the defect and thus keep a certain yield of products for stably producing a semiconductor element or a flat display device represented by the liquid crystal display device, which are expected to be further miniaturized even more in the future.

To keep the yield of products, it is necessary to determine whether a detected defect such as foreign substance has influence on the yield or not, and it is important to obtain information of a position where the defect such as foreign substance was detected, and information of size of the detected defect.

As a technique for calculating size of a defect detected by defect inspection apparatus, as described in JP-A-5-273110, a method is disclosed, in which a laser beam is irradiated to an object, and then scattering light from a particle on the object or a crystal defect therein is received and then subjected to image processing, thereby size of the particle or the crystal defect is measured. In "Yield Monitoring and Analysis in Semiconductor Manufacturing" mentioned in digest of ULSI technical seminar, pp 4-42 to 4-47 in SEMIKON Kansai in 1997, a yield analysis method using a defect by a foreign substance detected on a semiconductor wafer is disclosed.

SUMMARY OF THE INVENTION

As described above, inspection apparatus in the related art for various fine patterns including a pattern in a semiconductor device is now hard to satisfy detection accuracy of defect size required for detection of a defect on an increasingly miniaturized pattern. Therefore, it is desirable to accurately calculate size of a detected defect.

Defect inspection apparatus according to embodiments of the invention includes a unit for classifying defects into a plurality of classes based on feature quantity of the defects at detection, and modifying a size calculation method of a defect for each of classes.

That is, in embodiments of the invention, defect detection apparatus for detecting a defect of an object is configured to have an illumination unit for illuminating light to the object; a detection unit for detecting scattering light from the object; a defect detection unit for detecting the defect by processing a detection signal of the scattering light detected by the detection unit; a size measuring unit for calculating size of the defect detected by the defect detection unit; a size correction unit for correcting the size of the defect detected by the size measuring unit depending on separately obtained information of feature quantity or a type of the defect; a data processing unit for processing a result corrected by the size correction unit; and a display unit for displaying information of a result processed by the data processing unit.

According to embodiments of the invention, size of a detected defect can be accurately calculated, and for example, only defects having a size larger than a size to be managed can be extracted in semiconductor manufacturing. Thus, since a defect having higher influence on a production yield can be preferentially managed, productivity is improved in semiconductor manufacturing.

BRIEF DESCRIPTION OF THE DRAWINGS

These and other objects, features and advantages of the invention will be apparent from the following more particular description of preferred embodiments of the invention, as illustrated in the accompanying drawings.

FIGS. 2A to 2B are graphs showing examples of defect detection signals, wherein FIG. 2A shows a case of large signal intensity, and FIG. 2B shows a case of small signal intensity;

FIGS. 3A to 3B are views showing processing for each region, wherein FIG. 3A shows an example of dividing the inside of a die (chip), and FIG. 3B shows an example of dividing a front face of a wafer;

FIGS. 4A to 4B are scatter diagrams of defect size, wherein FIG. 4A shows an example of large dispersion, and FIG. 4B shows an example of small dispersion;

FIGS. 5A to 5B are views showing examples of representative values of defect size, wherein FIG. 5A shows an example of X or Y size, and FIG. 5B shows an example of L size;

FIGS. 8A to 8C are views showing examples of size correction using defects of which the size is known, wherein FIG. 8A shows a condition that the defects of which the size is known are disposed on a wafer, FIG. 8B shows a condition that size measured by SEM does not comparatively correspond to size detected and calculated by the defect inspection apparatus in a scatter diagram of defect size, and FIG. 8C shows a condition that the calculated size comparatively corresponds to the size measured by SEM by changing a slope of a graph by changing a factor when size of a defect detected by the defect inspection apparatus is calculated, in the scatter diagram of defect size;

FIGS. 10A to 10C are views showing correction examples when a defect signal is saturated, wherein FIG. 10A is a graph showing a condition that the defect signal is not saturated, FIG. 10B is a graph showing a condition that the defect signal is saturated, and FIG. 10C is a view showing a method of predicting a peak value of a signal when a detection signal is saturated;

FIGS. 11A to 11B are scatter diagrams of defect size, wherein FIG. 11A shows a condition that size measured by SEM does not comparatively correspond to size detected and calculated by the defect inspection apparatus.

FIGS. 14A to 14B are graphs showing examples of a method of extracting a defect signal and feature quantity, wherein FIG. 14A shows a case of using a threshold obtained by a normal threshold setting method, and FIG. 14B shows a case of setting a threshold lower than a normal threshold;

FIGS. 16A to 16B are view of an example of an illumination optical system, wherein FIG. 16A is a front view, and FIG. 16B is a side view.

DESCRIPTION OF THE PREFERRED EMBODIMENT

Figure 1:
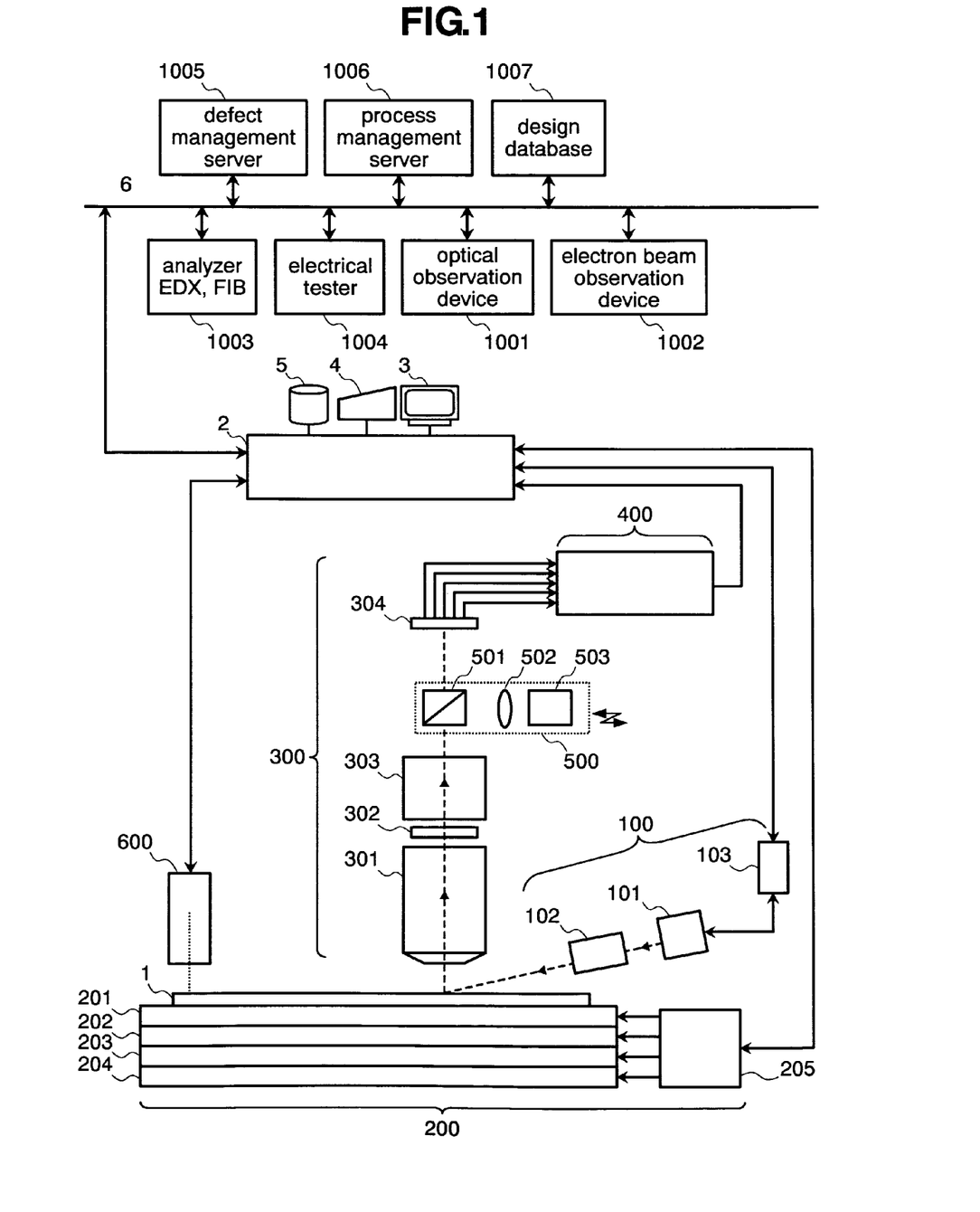
FIG. 1 is a block diagram showing a schematic configuration of defect inspection apparatus according to embodiments of the invention.

FIG. 1 shows an example of a configuration of inspection apparatus according to embodiments of the invention (hereinafter, mentioned as defect inspection apparatus).

The defect inspection apparatus is configured to have an illumination system 100, a stage system 200, a detection system 300, a Fourier transform surface observation system 500, a signal processing section 400, an observation optical system 600, and a control section 2.

Defect detection using the defect inspection apparatus shown in FIG. 1 is performed according to the following procedure. The illumination system 100 illuminates a wafer 1 set in the stage system 200, and the detection system 300 acquires an image of the illuminated wafer 1. The illumination system 100 adjusts output of a light source 101 by an illumination controller 103 according to an instruction value of the control section 2. As the light source 101, a laser light source is used, which emits laser in an ultraviolet region having a wavelength of 400 nm or less. The illumination system 100 includes a unit (not shown) for reducing coherency of the laser emitted from the laser light source. Illumination light is shaped into an appropriate form on the wafer 1 by an optical system 102. The stage system 200 includes a rotation stage 201, a Z stage 202, an X stage 203, and a Y stage 204, and moves with respect to the detection system 300 so that the detection system 300 can scan the whole surface of the wafer 1.

The detection system 300 includes a Fourier transform lens 301, spatial filter 302, focusing lens 303, and sensor 304. Here, the spatial filter 302 is to shield a diffraction light pattern caused by diffraction light from a repetitive pattern on the wafer 1, and set on the Fourier transform surface of the Fourier transform lens 301. A light shielding pattern of the spatial filter 302 is set such that a diffraction pattern of the wafer 1 is shielded, the diffraction pattern being observed by the Fourier transform surface observation system 500 having a structure that can be inserted and removed into/from an optical path of the detection system 300. That is, the system 500 is inserted into an optical path of the detection system 300 while removing the spatial filter 302, and then the optical path is branched by a beam splitter 501, and an image on the Fourier transform surface of the Fourier transform lens 301 is taken by a camera 503 via a lens 502 and observed. The light shielding pattern of the spatial filter 302 can be set for each type of an object or each of steps. The light shielding pattern of the spatial filter 302 may be fixed during wafer scan, or may be changed in real time depending on a region under scanning.

An image acquired by the detection system 300 is subjected to AD conversion and then transferred to the signal processing section 400, wherein the image is processed to detect a defect. The defect inspection apparatus further includes CPU 2, a display device 3, an input unit 4, and a storage device 5, thereby it can set any optional condition for inspection, and can store and display an inspection result or an inspection condition. Moreover, the defect inspection apparatus can be connected to a network 6, thereby the inspection result, layout information of the wafer 1, a lot number, the inspection condition, or an image of a defect observed by an observation device or data of a defect type can be shared over the network 6. Moreover, the defect inspection apparatus includes the wafer observation system 600 in order to allow observation of the detected defect or an alignment mark integrally formed on the wafer 1 for alignment of a pattern formed on the wafer 1. Furthermore, while not shown, it includes an automatic focusing unit, so that a region where an image is taken in using a sensor when the wafer is scanned on the stage system 200 is within the depth of focus of the detection system 300.

Figure 2A:
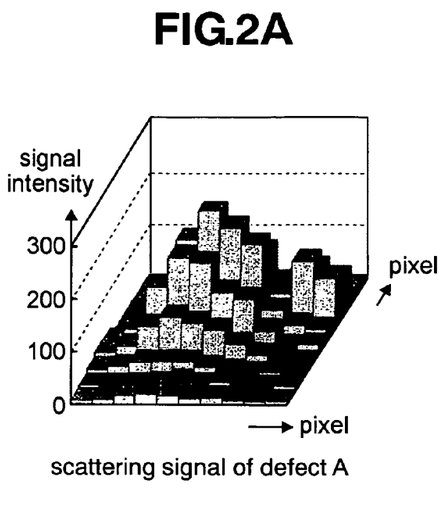
Figure 2B:
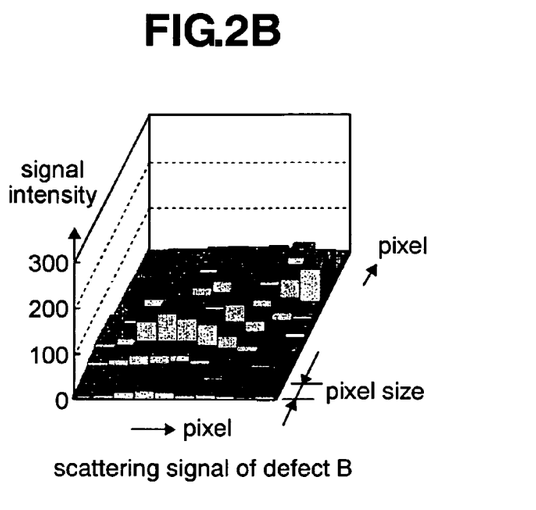

FIGS. 2A to 2B show three-dimensional display of examples of signal detection of two types of defects A and B respectively. FIGS. 2A to 2B exemplify defects having different signal intensity detected by the defect inspection apparatus while having the same size. A vertical direction represents signal intensity, showing intensity for each pixel. Even if defects (foreign substances) have the same size in SEM (scanning electron microscope) observation, detection signals in the defect inspection apparatus may be varied depending on a defect type, defect position, and surface pattern or surface material of the wafer 1. Thus, size of defects obtained through detection by the defect inspection apparatus according to embodiments of the invention are corrected based on information of the defect type, defect position, and surface pattern or surface material of the wafer 1, thereby size calculation accuracy of defects can be improved.

Moreover, to improve the size calculation accuracy of a defect, it is important to modify a detection condition depending on a position of the defect. Thus, in the defect inspection apparatus according to embodiments of the invention, grouping is carried out depending on fineness of a pattern in a detection portion of the wafer 1 or each of many dies (chips) formed on the wafer 1, so that a detection condition of the defect can be modified.

Figure 3A:
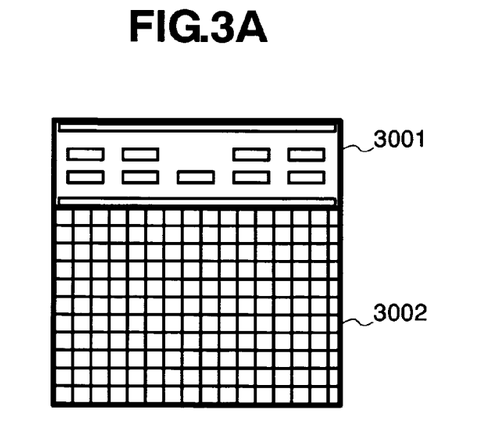
Figure 3B:
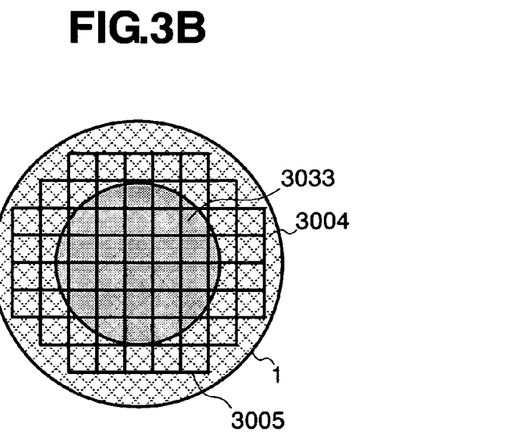

FIGS. 3A to 3B show examples of grouping for each of regions in the wafer or die (chip). FIG. 3A shows an example of grouping the inside of the die depending on a type of a circuit pattern. A reference 3001 shows a region where a wiring pattern is random in the die, and a reference 3002 shows a region where the wiring pattern is repeated at a constant pitch. FIG. 3B shows an example of grouping of the whole surface of the wafer 1. A reference 3003 indicates a central portion of the wafer 1, and a reference 3004 indicates the outer circumferential portion of the wafer. A reference 3005 indicates a die. In the case of a fine pattern, interference of illumination light may occur due to a pattern near a defect and the defect, and thus a detection signal of a defect may be different from that in the case of detecting a defect near a coarse pattern, and therefore grouping is carried out depending on regions. Moreover, when thickness is uneven in a wafer surface due to deposition, etching, or polishing, since a detection signal of a defect may be varied due to interference of light as well, grouping is carried out.

Figure 4A:
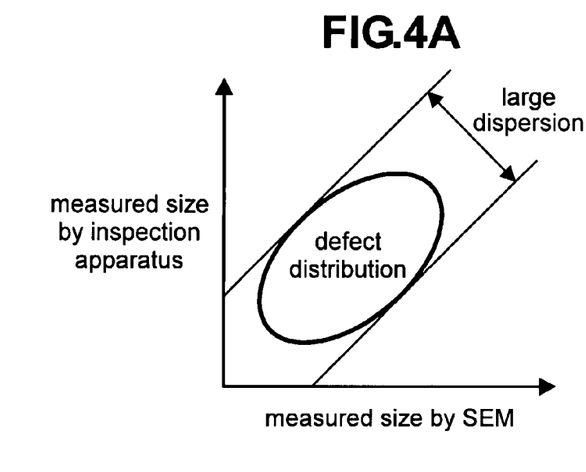
Figure 4B:
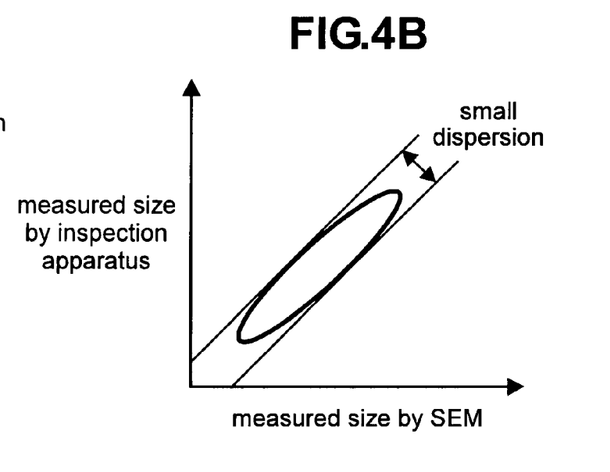

FIGS. 4A to 4B show an evaluation method of dimension accuracy of a defect. A graph is displayed on a screen, in which measured values of size by defect observation apparatus such as SEM are plotted as a horizontal axis, and calculated values of size by the defect inspection apparatus are plotted as a vertical axis, which allows visual expression of calculation accuracy of defect size. FIG. 4A shows an example of large dispersion of defect distribution, that is, low dimension accuracy. FIG. 4B shows an example of small dispersion of defect distribution compared with the example of FIG. 4A, that is, high dimension accuracy.

Figure 5A:
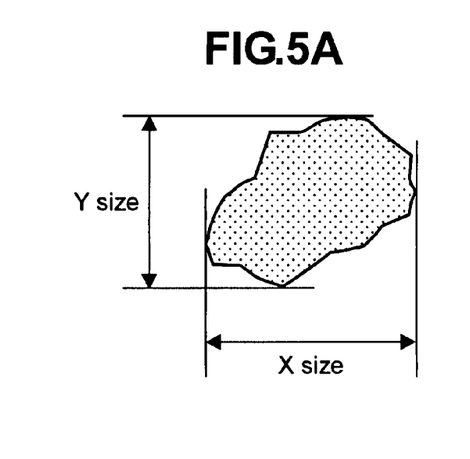
Figure 5B:
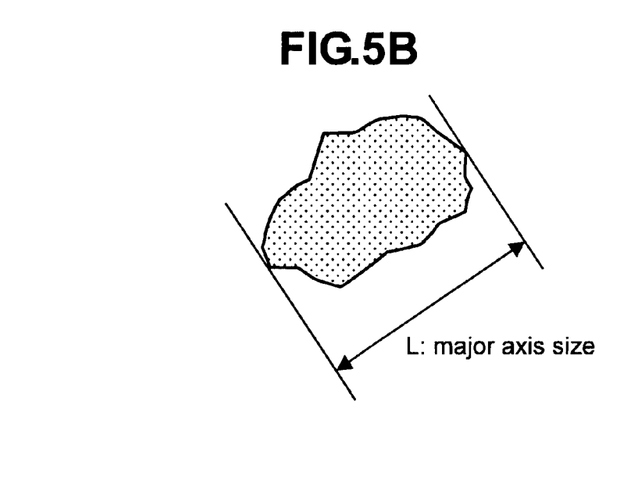

FIGS. 5A to 5B are views for illustrating a way of defining a measured value when defect size is measured by the defect observation device such as SEM. X and Y are coordinate axes used in observation of a defect by SEM. In a way of expressing the defect size, projected length in an X-axis direction (X size), projected length in an Y-axis direction (Y size), diameter of a circumscribed circle of a defect (L; major axis size), $\sqrt{(X+Y)}$, or $\sqrt{(X^2+Y^2)}$ can be used as a representative value. In yield management, one of the diameter of the circumscribed circle of the defect (L; major axis size), $\sqrt{(X+Y)}$, and $\sqrt{(X^2+Y^2)}$, or a combination of them is used.

Figure 6:
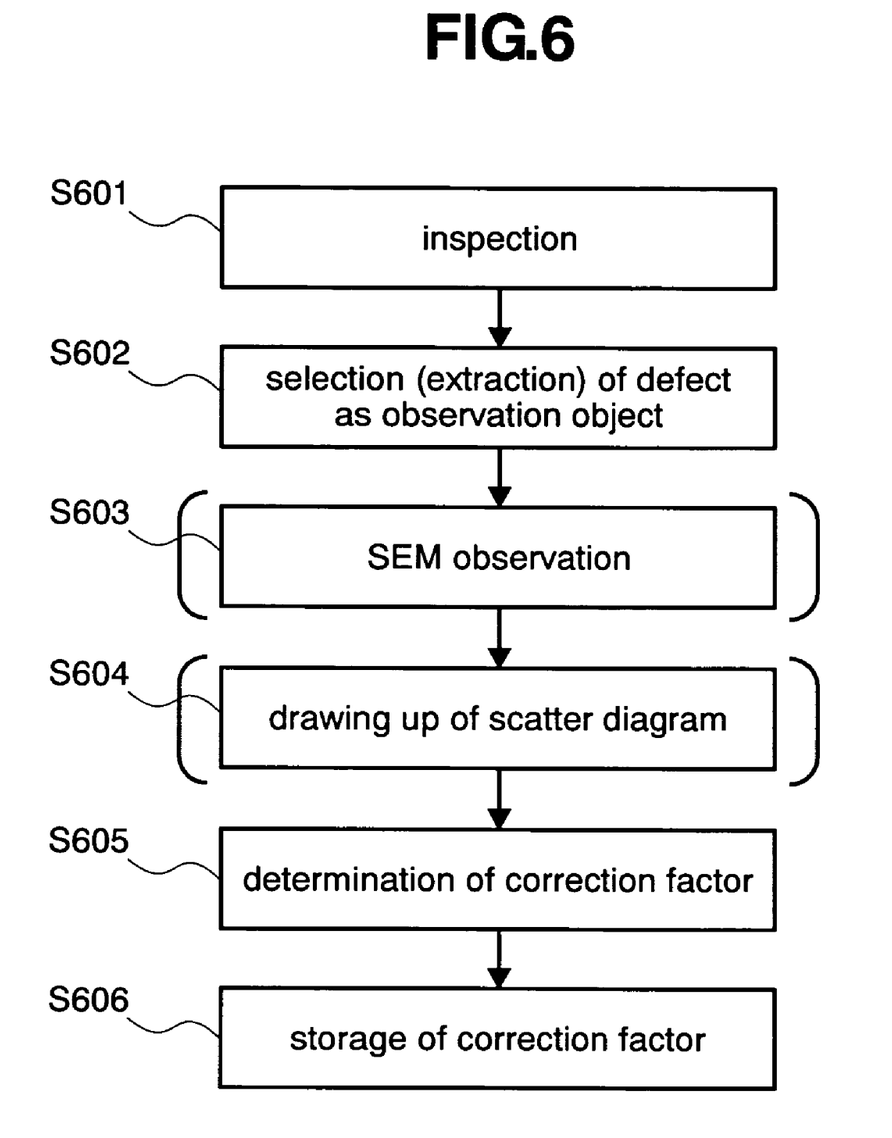
FIG. 6 is a flowchart of setting a correction factor of size calculation.
Figure 7:
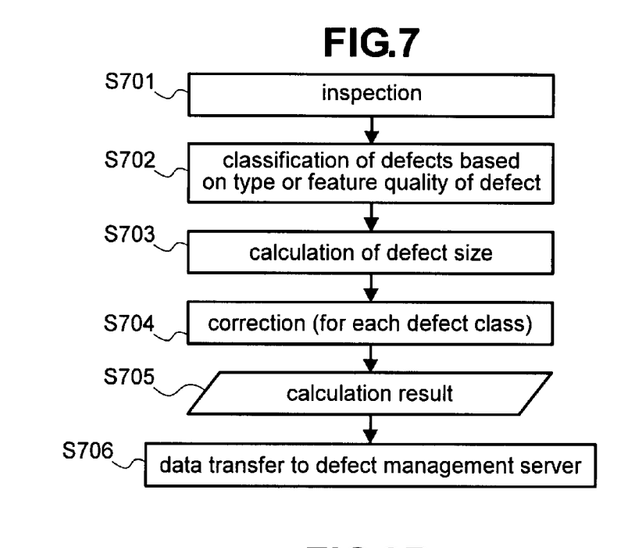
FIG. 7 is a flowchart of inspection and output.

FIG. 6 shows a condition setting flow for correcting size of a defect detected by the defect inspection apparatus. In embodiments of the invention, a correction factor that was determined and stored according to the flow of FIG. 6 is used, and size of a defect on the wafer, which was inspected and detected by the defect inspection apparatus according to a flow shown in FIG. 7, is calculated, and then inspection data added with size is registered into a defect management server.

A flow of FIG. 6 is described below. Inspection is performed using the defect inspection apparatus in S601, and defects to be observed by the defect observation apparatus such as SEM are selected from defects detected using the defect inspection apparatus in S602. When the number of defects is small, for example, about 100, the whole number of them may be selected. When the number of defects is large, while they may be randomly extracted, if defects to be observed are extracted using SSA (Spatial Signature Analysis) based on a distribution condition in a wafer plane, several types of defects in a wafer can be evenly extracted. After defects as objects are selected in S602, size or a type (convex defect, concave defect, planar defect or the like) of the defect as object selected by the defect observation apparatus such as SEM is obtained in S603. After that, based on information of the size or type of the defect, a size calculation result of the defect inspection apparatus is compared with a measurement result of the defect observation apparatus such as SEM to create a scatter diagram as shown in FIG. 4 in S604, then a correction factor is determined depending on the size or type of the defects in S605, and then stored in S606.

Comparison between the size calculation result of the defect inspection apparatus and the measurement result of the defect observation apparatus such as SEM in S604 can be carried out by the defect inspection apparatus, SEM, a separated personal computer or the like. Since creation of the scatter diagram in S604 is intended to be for reference when a user adjusts a condition, in the case that the correction factor is automatically calculated, it need not always be shown diagrammatically. In correction in S605, linear correction (y=ax+b): (x is defect size calculated by the defect inspection apparatus, y is size after correction, a is a correction factor, and b is an offset value) may be used, or a higher-order transformation equation may be used for the correction. Regarding a way of determining the correction factor a or the offset value b, one of a value previously registered into the defect inspection apparatus, a value adapted for each treatment step in wafer manufacturing, and a value corresponding to a defect type or feature quantity of a defect, or a combination of them may be used.

After the correction factor has been calculated in S605, the correction factor is stored in S606, consequently condition setting for size calculation is completed.

FIG. 7 shows a flow of inspection and output. A wafer is inspected (S701), then classification of defects is performed based on a defect type or feature quantity of a defect (S702). Defect size is calculated in S703, and then size is corrected for each defect class using the correction factor previously set according to the flow described using FIG. 6 in S704. A size calculation result S705 after correction is added to the defect detection result, then data of them are transferred to a defect management server (S706).

Figure 8A:
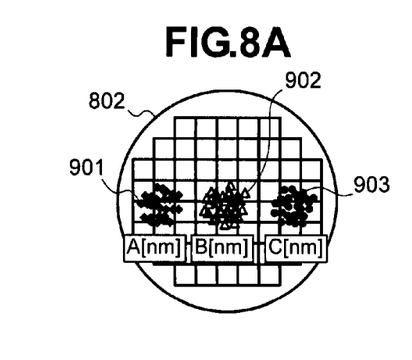
Figure 8B:
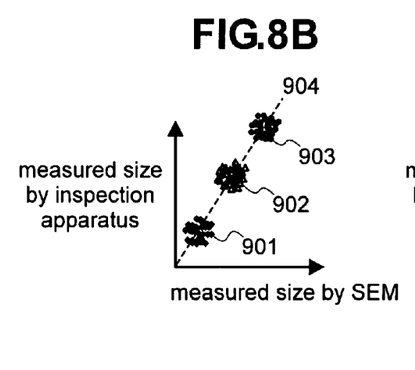
Figure 8C:
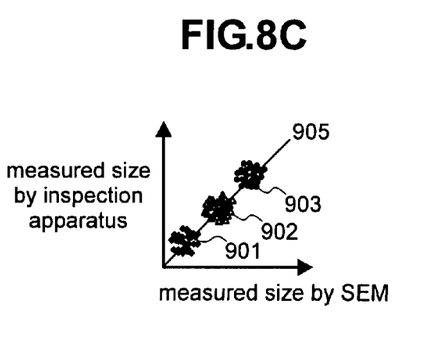

FIGS. 8A to 8C show a method of size calibration using a defect having known size. FIG. 8A shows a standard wafer in which the defects having known size are integrally formed, or a product wafer, dummy wafer, or mirror wafer on which standard particles are scattered, wherein defects 901 (size A (nm)), 902 (size B (nm)), and 903 (size C (nm)) having known size are integrally formed.

FIG. 8B shows an aspect that the size detected and calculated by the defect detection apparatus is different from the size measured by SEM depending on a surface condition or surface material of a wafer due to an adjustment condition of the defect detection apparatus or difference in machine, indicating a relationship between actual size of the defects 901, 902 and 903 having known size, which were measured using SEM, and size of the defects detected and calculated by the defect detection apparatus. A reference 904 indicates an approximate curve. Based on the approximate curve of 904, a factor in size calculation is changed so that a slope of a graph is corrected to be approximately 45 degrees (FIG. 8C), thereby a value of the defect size detected and calculated by the defect detection apparatus can be calibrated.

Figure 9:
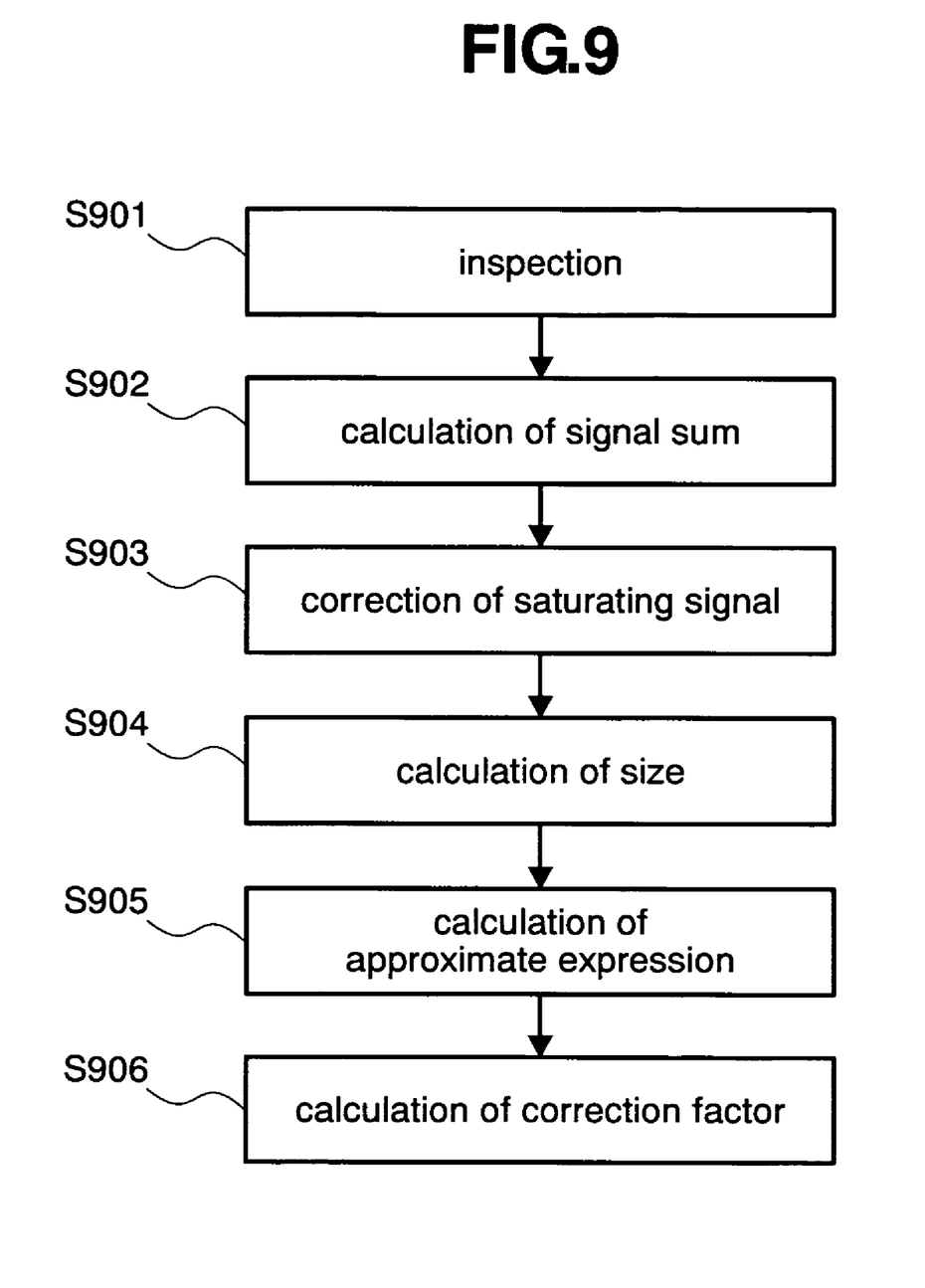
FIG. 9 is a flowchart of calculating a correction factor of size.

FIG. 9 shows a flow of obtaining a factor for correcting size. First, a wafer is inspected to detect a defect using the defect inspection apparatus according to embodiments of the invention (S901), then a sum signal of detection signals in the whole region of the detected defect is calculated (S902). Since part of the detected defects may be beyond a dynamic range of the sensor 304, saturating signal correction (S903) is performed, and size is temporarily calculated (S904). In this time point, since the calculated size may be different from actual size measured by SEM, an approximate formula is then calculated (S905), and then a correction factor is calculated according to the approximate formula (S906). For correction, linear correction (y=ax+b): (x is defect size calculated by the defect inspection apparatus, y is size after correction, a is a correction factor, and b is an offset value) may be used, or a higher-order transformation equation may be used.

Figure 10A:
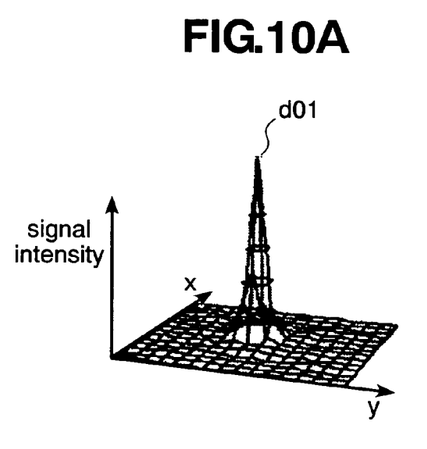
Figure 10B:
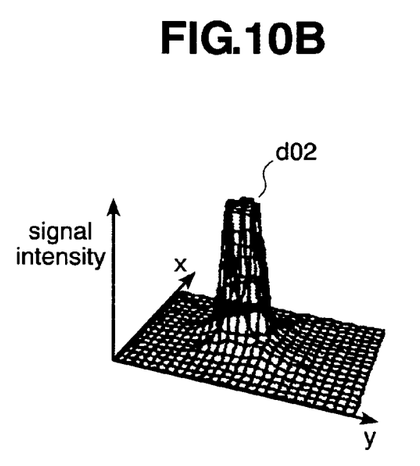
Figure 10C:
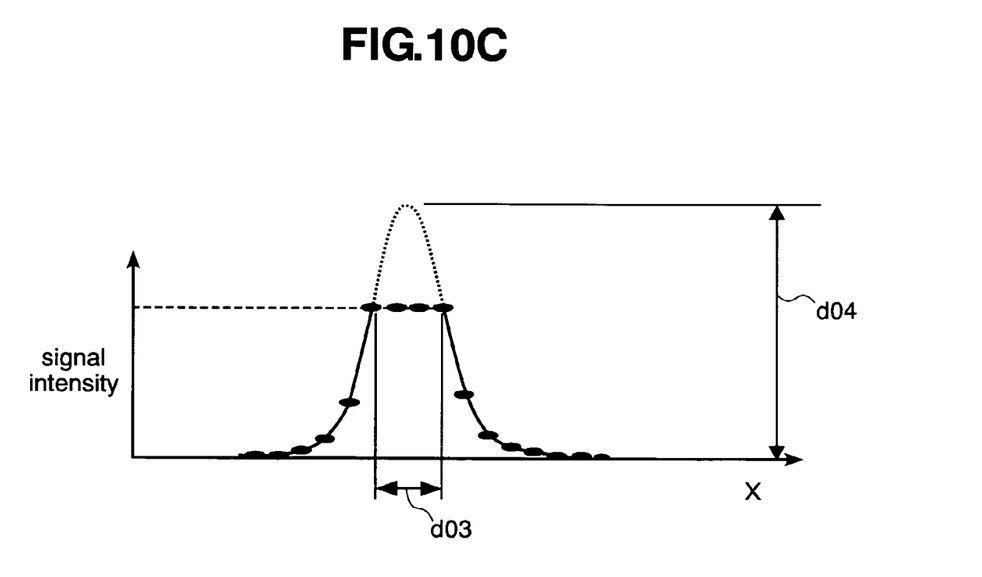

FIGS. 10A to 10C show a specific example of the saturating signal correction of the step S903 in FIG. 9. FIG. 10A shows an example of a defect of which the signal is not saturated, wherein d01 indicates a signal peak. FIG. 10B shows signal intensity (d02) of a defect of which the signal is partially beyond a dynamic range of a sensor during detection of a defect signal and thus saturated. As shown in FIG. 10C, a portion where a defect signal is lacked because of saturation is approximated by an appropriate function, so that a signal of a lacked portion is estimated, thereby a saturating signal can be corrected. For example, when a defect signal is approximated by Gaussian curve, a value of the number of saturated pixels (d03) and broadening of Gaussian distribution (standard deviation) are supposed, thereby a peak (d04) of the defect signal can be estimated.

Figure 11A:
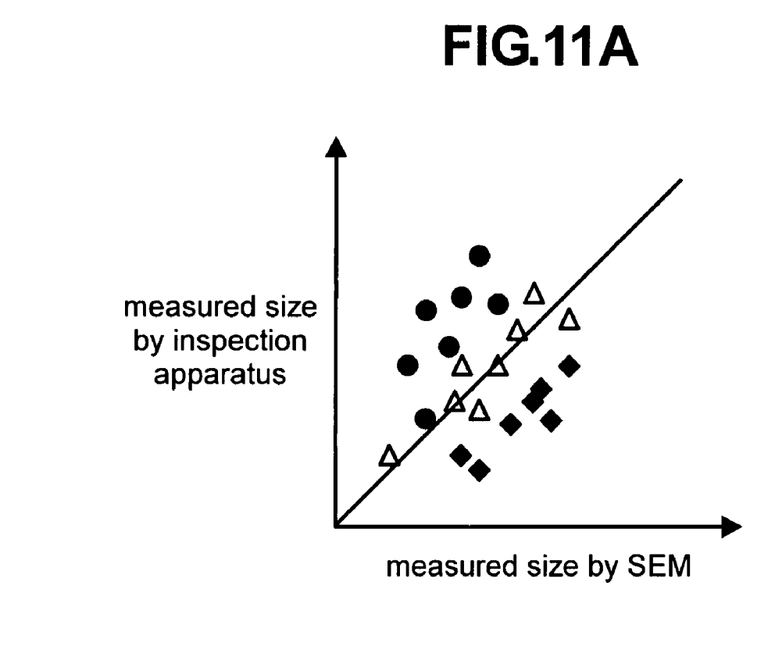
Figure 11B:
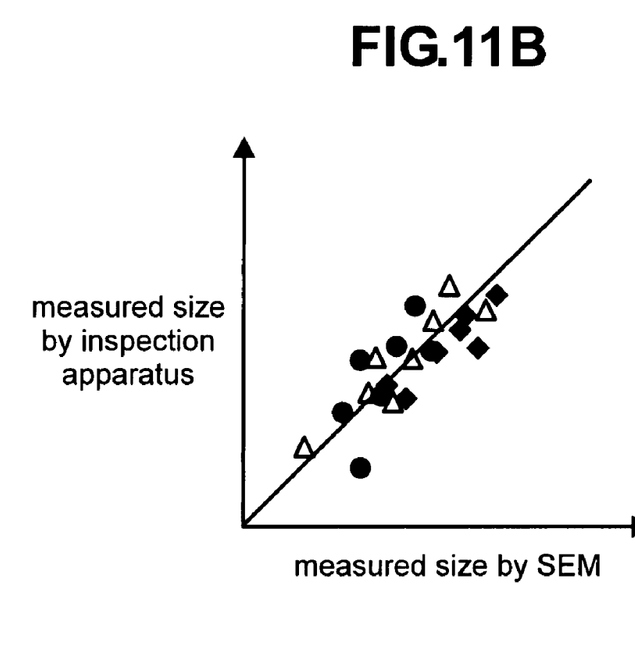
FIG. 11B shows a condition that size, which was calculated with performing correction to a defect detected by the defect inspection apparatus based on feature quantity of the defect, comparatively corresponds to the value measured by SEM.

FIGS. 11A to 11B show correction based on feature quantity of a defect. A correction factor is obtained according to a procedure shown in FIG. 6 for each defect type (convex defect, concave defect, planar defect or the like), then a correction factor of defect size is modified based on feature quantity of a defect according to a procedure of FIG. 7, thereby dimension accuracy can be improved. FIG. 11A is a scatter diagram of defect size, showing a condition that size measured by SEM does not comparatively correspond to size detected and calculated by the defect inspection apparatus. On the contrary, FIG. 11B is a scatter diagram of defect size in a condition that size, which was calculated with performing correction based on feature quantity of a defect (for example, defect size) to a defect defected by the defect inspection apparatus, comparatively corresponds to size measured by SEM. Size may be calculated by obtaining the correction factor for each defect type (convex defect, concave defect, planar defect or the like), rather than the feature quantity of a defect.

While a procedure of temporarily obtaining size before correction is shown here, size may be calculated at a time during size calculation using information such as feature quantity of a defect or the defect type. For this purpose, information on defects such as feature quantity of a defect or a defect type can be treated as a variable in a size calculation formula in size calculation.

Figure 12:
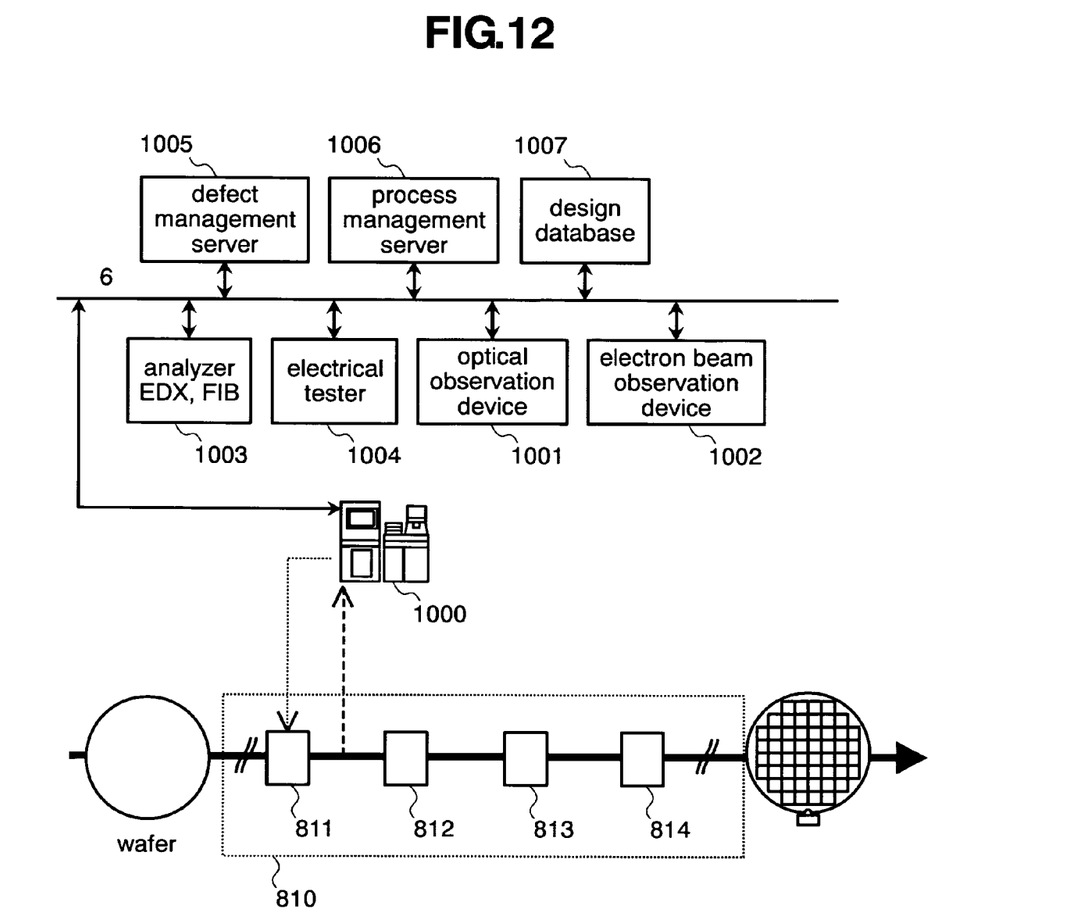
FIG. 12 is a block diagram showing a relationship between a manufacturing process and inspection apparatus.

FIG. 12 shows a relationship between the defect inspection apparatus according to embodiments of the invention and a semiconductor manufacturing process. A wafer after passing through a particular step is inspected by the defect inspection apparatus according to embodiments of the invention. In a manufacturing process 810, for example, inspection is carried out after a photolithography step (810). After the inspection, a defect is observed by review apparatus 1001 or 1002, so that a cause of the defect is estimated from a type, size, or a shape of the defect to find a step where the defect is caused, thereby a manufacturing device in the relevant step is managed. When the cause of the defect is not found only by defect observation, element analysis by an analyzer 1003 or observation of a section profile of the defect is performed for further detailed investigation to search the cause of the defect. As described above, a yield of the semiconductor device is improved by repeating inspection and measures, consequently reliable semiconductor device can be manufactured.

Figure 13:
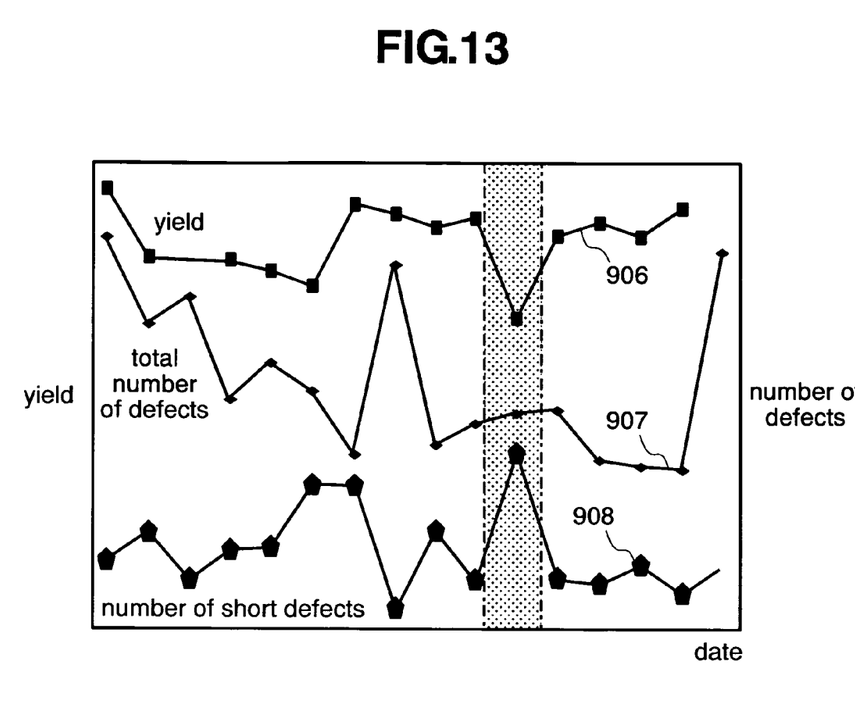
FIG. 13 is a graph showing a relationship between yield and the number of detected defects.

FIG. 13 shows a relation between the number of defects and a yield of a semiconductor product. A reference 906 indicates transition of the yield of the semiconductor product, a reference 907 indicates transition of total detection number of defects in a particular step. A reference 908 indicates transition of the number of a particular type of defects (in this case, short-circuit defect). While the yield 906 is significantly decreased in a hatched period in FIG. 13, the total detection number 907 is increased only slightly. When the detected defects are classified, and the number of short-circuit defects is noticed, it is known that the short-circuit defects are increased in the period where the yield is decreased. In addition to the total number of defects, defects are classified, and the number is monitored for each defect type, thereby information in correlation with the yield of the semiconductor product can be obtained. The number of defects of which the size is at least management size may be noticed and managed by using a defect size calculation value rather than the defect type. The management size is determined based on a wiring rule in an inspection step. While not shown, criticality of the defect may be calculated from the defect size, defect type, and wiring rule to monitor the number of defects having at least a certain value of criticality.

Figure 14A:
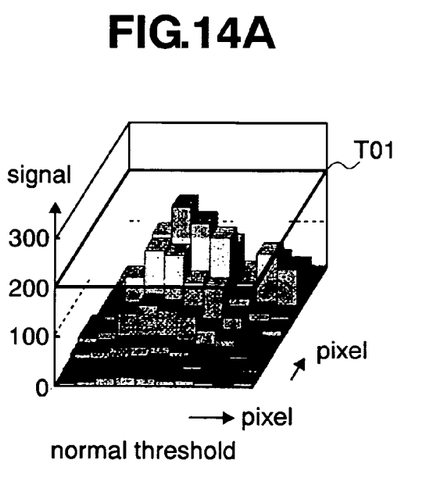
Figure 14B:
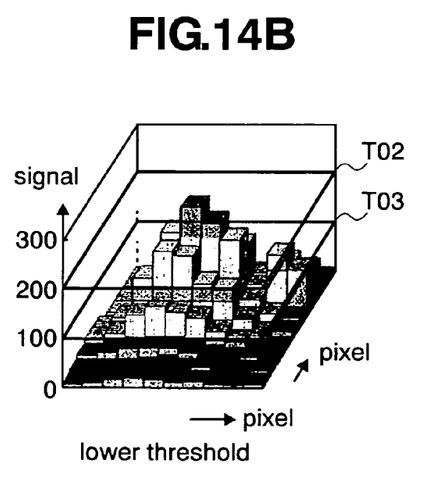

FIGS. 14A to 14B are conceptual diagrams of defect detection thresholds T01, T02 and a feature-quantity extraction threshold T03. FIG. 14A shows an example where the defect detection threshold T01 is equal to the feature-quantity extraction threshold T03. In inspection of a semiconductor wafer, the defect detection threshold T01 is normally set high to suppress false detection of a normal portion. Therefore, in FIG. 14A, only a part of defect signals can be used. Thus, as shown in FIG. 14B, the feature quantity is extracted with a threshold (T04) lower than the defect detection threshold T02, thereby more effective extraction of the feature quantity can be performed.

Figure 15:
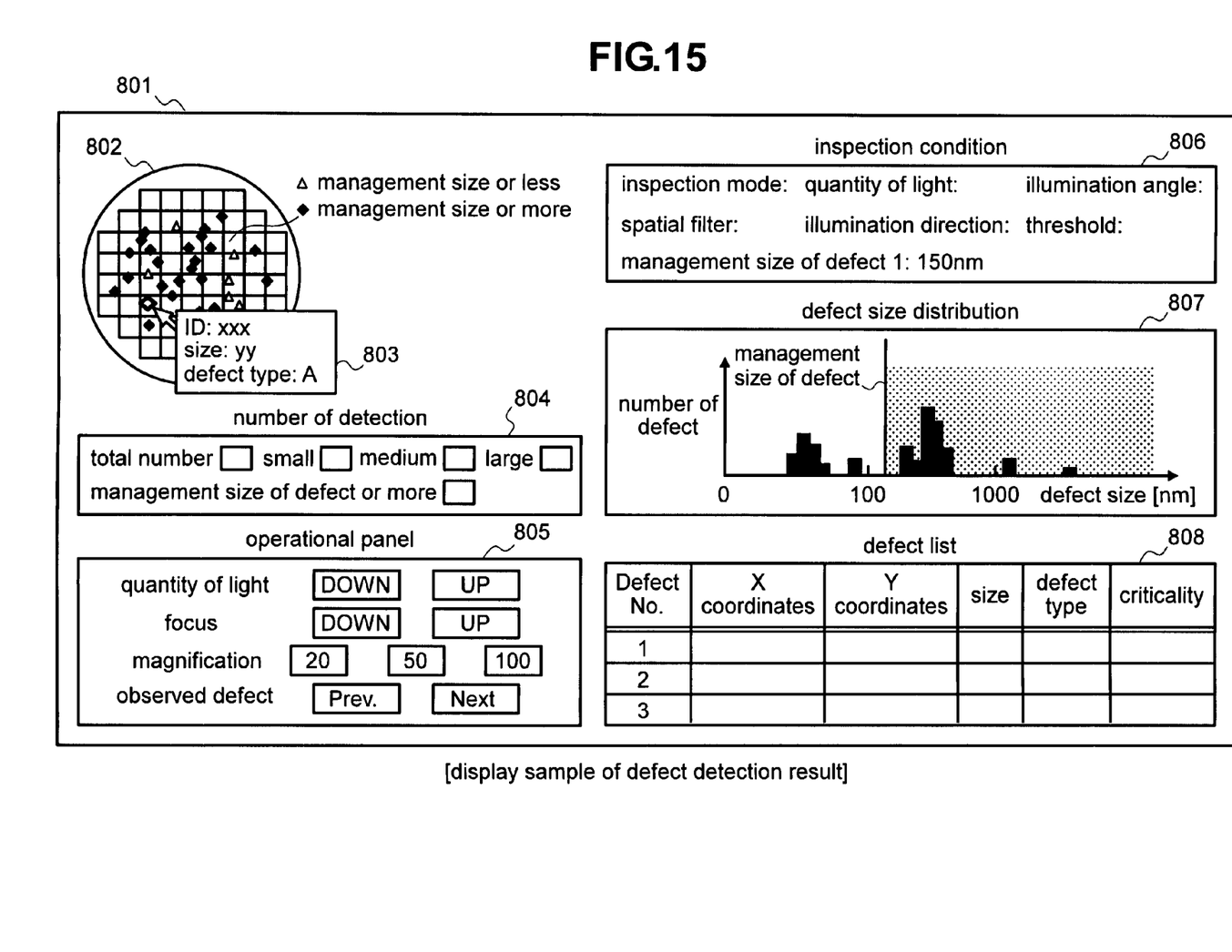
FIG. 15 is a front view of a display screen showing a screen display example of the defect inspection apparatus.

FIG. 15 shows a display example of a defect detection result. A reference 801 indicates an example of a display screen. In a defect map (802), display is classified depending on whether defect size is at least a defect management size determined at setting of inspection conditions or not, thereby trouble occurrence and a level of influence on the yield can be instinctively determined. Moreover, defect display is clicked by a mouse, thereby defect ID, size (calculation value of the defect inspection apparatus), a defect type and the like can be shown (803).

Moreover, a graph showing frequency of defect occurrence is displayed for each defect size (807), thereby the trouble occurrence and the level of influence on the yield can be also instinctively determined.

On the screen, a region 804 for displaying the total number of detected defects or the number of the defects for each size, a region 805 for displaying an operational panel, a region 806 for setting a inspection condition, a region 808 for displaying a defect list are also provided. The display regions may be displayed on one screen at the same time, or may be displayed on separated screens respectively, or several regions of them may be displayed in a combined manner.

Figure 16A:
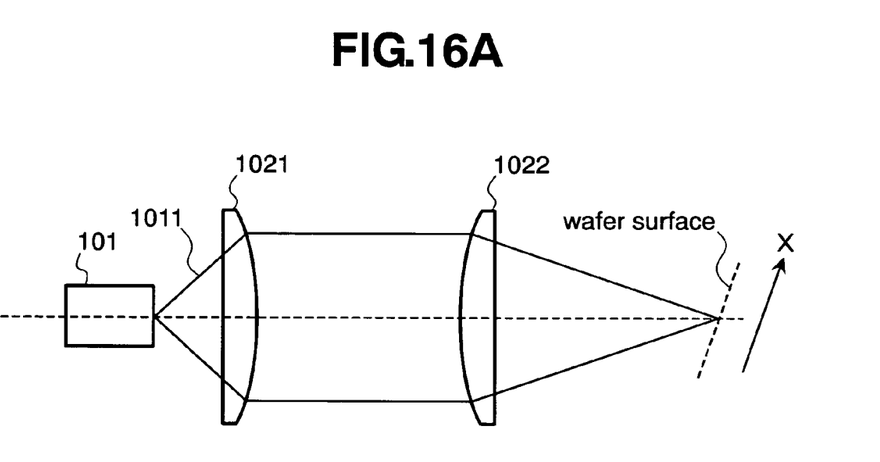
Figure 16B:
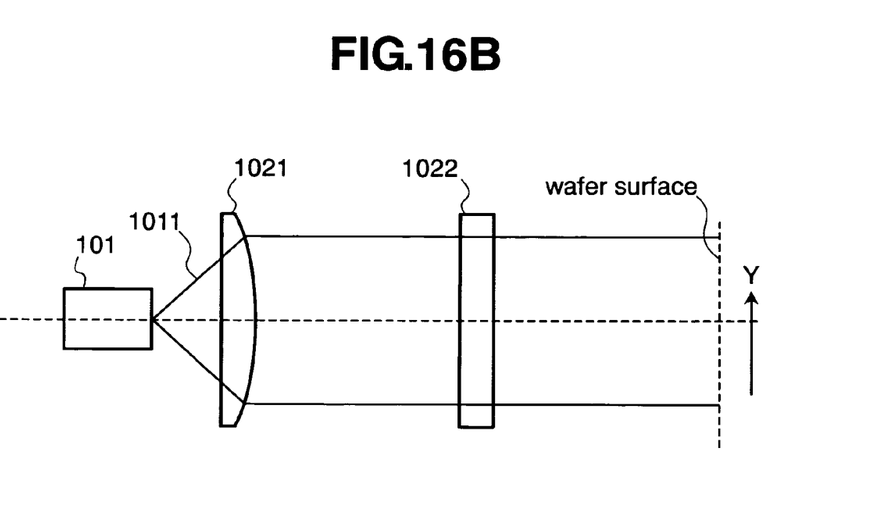

FIG. 16 shows an example of the illumination optical system 102 in the configuration of the defect inspection apparatus shown in FIG. 1. Here, an example where the light source 101 is a laser light source is shown. Laser 1011 emitted from the laser light source 101 is diverged at a certain divergence angle, and made into parallel light by a lens 1021, and then shaped to be one-sided condensing illumination by a cylindrical lens 1022 and then irradiated to a wafer surface. An illumination pattern is linear on the wafer surface, and used in a combined manner with scan of the stage, thereby a certain area of the wafer surface can be collectively detected. In this case, for the sensor 304, a linear sensor corresponding to the illumination area or a TDI sensor (Time Delay Integration Sensor) is preferably used. When the TDI sensor is used for the sensor 304, a signal detected by the TDI sensor is outputted in parallel from a plurality of taps of the TDI sensor, and the signals outputted in parallel are subjected to signal processing in parallel in the signal processing section 400, thereby defect detection speed can be improved. When the illumination pattern is a dot-like pattern, AOM, AOD, a galvanometer mirror or the like is used in the illumination optical system to allow scan by the dot-like illumination, and move-

The invention claimed is:

1. A defect inspection apparatus comprising:
an illumination unit for illuminating light to an object to be inspected,
a detection unit for detecting scattering light from the object to be inspected,
a signal processing unit for detecting a defect by processing a detection signal of the scattering light detected by the detection unit, and calculating size of the defect detected by the defect detection unit,
a size correction unit for correcting the size of the defect calculated by the size measuring unit depending on separately obtained information of feature quantity or type of the defect, and
a display unit for displaying information of a result processed by the signal processing unit,
wherein said signal processing unit further calibrating the size of the defect calculated by the calculating, by using a relationship between a size of a defect whose size is known and a size of the defect detected by the detecting unit and calculated by the signal processing unit.

2. The defect inspection apparatus according to claim 1:
wherein the illumination unit obliquely irradiates light shaped linearly to a surface of the object to be inspected.

3. The defect inspection apparatus according to claim 1:
wherein the illumination unit irradiates laser having a wavelength of less than 400 nm to the object to be inspected.

4. The defect inspection apparatus according to claim 1:
wherein the detection unit includes a spatial filter for shielding scattering light from a repetitive pattern formed on the object to be inspected in the scattering light from the object to be inspected, and a sensor for detecting scattering light which was not shielded by the spatial filter.

5. The defect inspection apparatus according to claim 1:
wherein the display unit displays information on positional information and size of a defect, a defect type, and criticality as the information of the result processed by the data processing unit.

6. The defect inspection apparatus according to claim 1:
wherein the light detection unit includes a TDI sensor that outputs detection signals in parallel, and the defect detection unit processes the signals outputted in parallel from the TDI sensor in parallel.

7. The defect inspection apparatus according to claim 2:
wherein the light detection unit includes a TDI sensor that outputs detection signals in parallel, and the defect detection unit processes the signals outputted in parallel from the TDI sensor in parallel.

8. A defect inspection method comprising steps of:
illuminating light to an object to be inspected,
detecting light scattered from the object to be inspected due to irradiation of the light,
detecting a defect by processing a detection signal of the scattered light,
calculating size of the detected defect,
correcting the size of the calculated defect by calibrating the calculated size of the defect using a relation between a size of a sample defect which is known and the size of the sample defect detected at the detecting step and calculated at the calculating step, and
displaying information relating to the corrected size of the defect on a screen.

9. The defect inspection method according to claim 8:
wherein in the step of illuminating light to the object to be inspected, said light is shaped linearly and is obliquely irradiated to a surface of the object to be inspected.

10. The defect inspection method according to claim 8:
wherein in the step of illuminating light to the object to be inspected, said light is a laser having a wavelength of less than 400 nm.

11. The defect inspection method according to claim 8:
wherein in the step of detecting light scattered from the object, light scattered from repetitive patterns formed on the object is shielded by a special filter, and light scattered from the object and not shielded by the spatial filter is detected by a sensor.

12. The defect inspection method according to claim 8:
wherein information on positional data and size of a defect, a defect type, and criticality is displayed as the information of the processed result.

13. The defect inspection method according to claim 8:
wherein in the step of detecting the scattering light, the scattering light is detected by a TDI sensor that outputs detection signals in parallel, and in the step of detecting the defect, the signals outputted in parallel from the TDI sensor are processed in parallel.

* * * * *